United States Patent [19]

Garg

[11] Patent Number: 4,840,184
[45] Date of Patent: Jun. 20, 1989

[54] SECOND METHOD FOR USING CANNULA INCLUDING A VALVE STRUCTURE AND ASSOCIATED INSTRUMENT ELEMENTS

[76] Inventor: Rakesh K. Garg, R.R. #1, Box 3032, Lafayette, N.J. 07848

[21] Appl. No.: 215,830

[22] Filed: Jul. 6, 1988

Related U.S. Application Data

[63] Continuation-in-part of Ser. No. 97,098, Sep. 16, 1987.

[51] Int. Cl.⁴ ............................................. A61B 10/00
[52] U.S. Cl. ..................................... 128/753; 128/754; 128/763; 604/169
[58] Field of Search ......................... 128/310, 751-754, 128/760, 763; 604/169

[56] References Cited

U.S. PATENT DOCUMENTS

| | | | |
|---|---|---|---|
| 1,086,873 | 2/1914 | Tyrrell | 604/182 |
| 1,740,174 | 12/1929 | Hevern | 27/24 A |
| 2,482,622 | 9/1949 | Kahn | 604/104 |
| 3,434,691 | 3/1969 | Hamilton | 251/184 |
| 3,777,737 | 12/1973 | Bucalo | 128/1 R |
| 3,783,900 | 1/1974 | Walbillig | 137/625.47 |
| 3,957,052 | 5/1976 | Topham | 604/236 |
| 4,051,852 | 10/1977 | Villari | 604/183 |
| 4,187,849 | 2/1980 | Stim | 604/236 |

*Primary Examiner*—Edward M. Coven
*Assistant Examiner*—Randy Citrin
*Attorney, Agent, or Firm*—R. Martin Oliveras

[57] ABSTRACT

According to the present invention, an outer hollow cannula including a valve structure is adapted to receive inner instrument elements for performing the procedures of thoracentesis and plueral biopsy. The cannula comprises: a hollow cylindrical body including a longitudinally directed circular lumen; proximal attachment means; and the valve structure being interposed along the length of the cannula lumen. The valve structure includes a cylindrical member being interposed perpendicularly along the path of the cannula lumen, being rotatable about an axis perpendicular to the longitudinal direction of the cannula lumen, and further includes a short lumen having the same diameter as the cannula lumen and being rotatable to be concentric with the cannula lumen or being rotatable to be perpendicular to the cannula lumen. For performing the thoracentesis procedure, the cannula also comprises a distal circular annular surface. The cannula is adapted to receive an inner hollow needle instrument element including proximal attachment means, a location surface marker, and a distal slanted elliptical annular surface. For performing the pleural biopsy procedure, the cannula also comprises a distal tapered circular sharp edge. The cannula is adapted to receive an inner solid stylet instrument element and an inner hollow cutting needle instrument element. The stylet includes proximal attachment means, a location surface marker, and a distal symmetrical tapered pointed edge. The cutting needle includes: proximal attachment means, a proximal location surface marker, a distal location surface marker, distal sharp edge cutting means, and a distal circular annular surface.

1 Claim, 5 Drawing Sheets

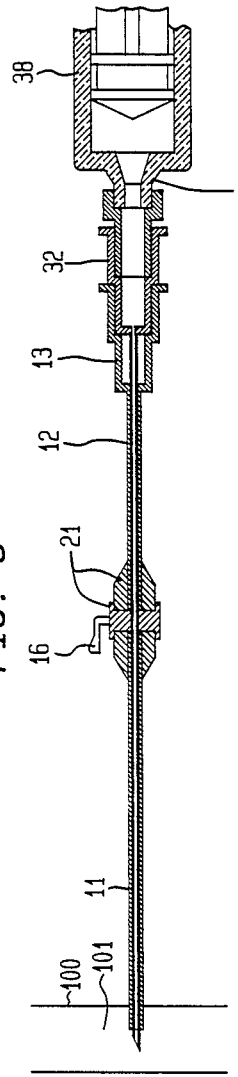
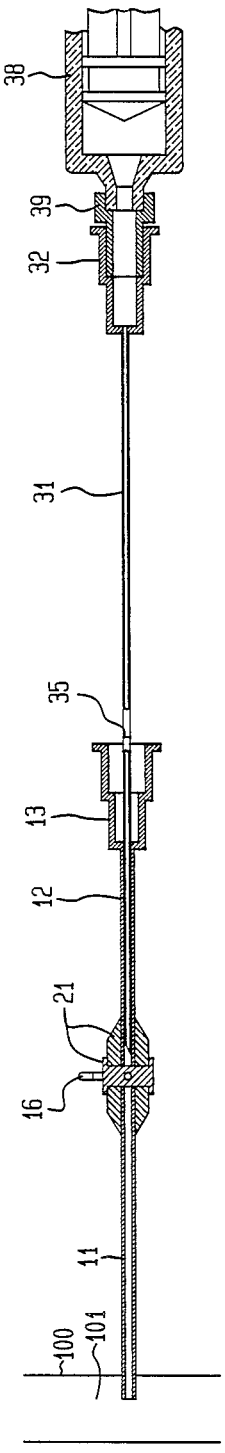
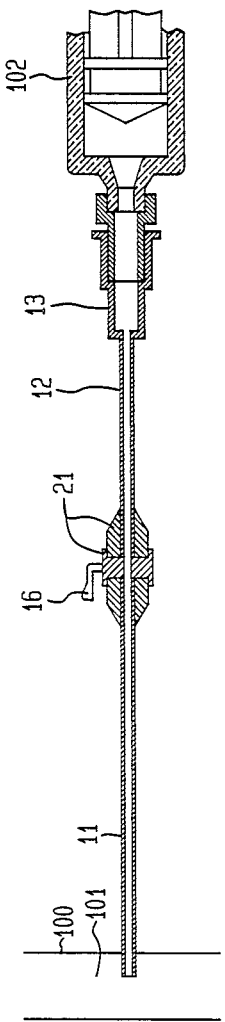
FIG. 3
FIG. 4
FIG. 5

SECOND METHOD FOR USING CANNULA INCLUDING A VALVE STRUCTURE AND ASSOCIATED INSTRUMENT ELEMENTS

FIELD OF THE PRESENT INVENTION

This invention relates to medical and surgical instruments and in particular to a method for using a cannula including a valve structure and associated instrument elements for performing the procedures of pleural biopsy and thoracentesis.

OTHER RELATED APPLICATIONS

This application is a continuation-in-part application of copending application Ser. No. 07/097,098, filed 9/16/88, and entitled "Cannula Including A Valve Structure And Associated Instrument Elements And Method For Using Same" by the same applicant herein.

DISCUSSION OF THE PRIOR ART

The prior art discloses several medical and surgical instruments including valve structures such as:

a. Tyrrell U.S. Pat. No. 1,086,873 entitled "Syringe" discloses a device comprising an axially perforated conoidal head, a stop pin, a injection tube, connecting means, a rotary tapering valve stem, holding means, and a second pin;

b. Hevern U.S. Pat. No. 1,740,174 entitled "Embalmer's Trocar" discloses a device comprising an elongated tube, a trocar point, a pipe, three branch pipes, a valve, and a manually operated pipe;

c. Kahn U.S. Pat. No. 2,482,622 entitled "Self-Retaining Uterine Cannula" discloses such a cannula comprising a tubular shaft, a valve, a sealing acorn, an acorn stop, a tenaculum control member, and a thumb ring limiting member;

d. Hamilton U.S. Pat. No. 3,434,691 entitled "Valve" discloses such a valve comprising a body of plastic material, a rigid housing, a plastic tapered plug valve member, and resilient means;

e. Bucalo U.S. Pat. No. 3,777,737 entitled "Method And Device For Reversibly Interrupting Fluid Flow In A Living Being" discloses a valve comprising an elongated valve housing, movable means, barrier means, and filamentary means;

f. Walbillig U.S. Pat. No. 3,783,900 entitled "Stop Cock" discloses a medical valve comprising a generally cylindrical cup-shaped body, a plug, cooperating means, and a stiffening element;

g. Topham U.S. Pat. No. 3,957,052 entitled "Pumping-Syringe" discloses such a syringe comprising a barrel, a plunger, a valving structure, a first ball valve seat, a second ball valve seat, a first ball valve, a second ball valve, and a cannula;

h. Villari U.S. Pat. No. 4,051,852 entitled "Aspirating Device" discloses such a device comprising: a valve assembly including a first port, a second port, a passageway, one-way valve means, a third port, a second passageway, and second one-way valve means; port means; and pump means; and i. Stim U.S. Pat. No. 4,187,849 entitled "Suction Curettage Device With Valve Control And Support Means For Differing Diameter Tubes" discloses such a device comprising a housing and a suction tube support member.

It is apparent that the cited prior art patents do not disclose the cannula including the valve structure and associated instrument elements of the present invention for performing the procedures of a pleural biopsy and thoracentesis.

Objects of the present invention are therefore:

a. to provide a valve structure that is adaptable for performing either a pleural biopsy or a thoracentesis procedure;

b. to provide such a valve structure that allows communication with the pleural cavity for performing either a pleural biopsy or a thorcentesis procedure and to minimize the risk of a pneumothorax;

c. to provide such a valve structure that allows the deletion or addition of instrument elements through the proximal end of the cannula during the performing of either a pleural biopsy or a thoracentesis procedure while the cannula remains inserted into the pleural cavity;

d. to provide such a cannula including the valve structure that is adaptable to the insertion and extraction of various instrument elements through its proximal end; and e. to provide such a cannula including the valve structure that is adaptable to the attachment of syringe or other vacuum means at its proximal end.

SUMMARY AND FEATURES OF THE PRESENT INVENTION

A summary and features of the present invention are that:

a. an outer hollow cannula including a two-position valve structure is adapted to receive inner instrument elements for performing the procedures of thoracentesis and plueral biopsy;

b. such cannula comprises a hollow cylindrical body including a longitudinally directed circular lumen, proximal attachment means, and such valve structure being interposed along the length of such cannula lumen; such valve structure including a cylindrical member being interposed perpendicularly along the path of such cannula lumen and being rotatably about an axis perpendicular to the longitudinal direction of such cannula lumen, and also including a short lumen having the same diameter as such cannula lumen and being rotatable to be concentric with such cannula lumen or being rotatable to be perpendicular to such cannula lumen;

c. for performing the thoracentesis procedure, such cannula also comprises a distal circular annular surface and is adapted to receive an inner hollow needle instrument element including proximal attachment means, a location surface marker, and a distal slanted elliptical annular surface;

d. for performing the pleural biopsy procedure, such cannula also comprises a distal tapered circular sharp edge and is adapted to receive an inner solid stylet instrument element and an inner hollow cutting needle instrument element; such stylet including proximal attachment means, a location surface marker, and a distal symmetrical tapered pointed edge; and such cutting needle including proximal attachment means, a proximal location surface marker, a distal location surface marker, distal sharp edge cutting means, and a distal circular annular surface;

e. such valve structure is in the open position when such associated instrument element is in the fully inserted position within such cannula; and f. such valve structure is in the closed position when such associated instrument element is fully extracted from such cannula.

Advantages of the present invention are therefore that:

a. the cannula including the valve structure is adaptable to receive instrument elements used for performing either a pleural biopsy or a thoracentesis procedure;

b. the cannula including the valve structure may be utilized for performing either a pleural biopsy or a thoracentesis procedure without having to remove the cannula from the pleural cavity during the respective procedure;

c. use of the cannula including the valve structure lessens the probability of pneumothorax during the respective procedure;

d. the cannula including the valve structure is adaptable for use with respect to any part of the body where it is desirable to avoid leakage of gas or fluid into or from the body during the respective procedure;

e. use of the cannula including the valve structure does not require significant patient cooperation or significant physician skill for performing the respective procedure;

f. the cutting needle instrument element in combination with the cannula can be used with relative safety and will provide high yield in most patients including less cooperative patients and those with less pleural fluid; and g. use of the cannula including the valve structure in combination with the stylet and the cutting needle instrument elements significantly reduces the complication of pneumothorax.

DESCRIPTION OF THE DRAWING

The above and other objects, features, and advantages of the present invention will be better appreciated from a reading of the following detailed description in conjunction with the drawing in which:

FIG. 3 is a cross-sectional side view of the needle of FIG. 2 being fully inserted into the cannula of Figure 1 including the valve structure in the open position;

FIG. 4 is a partially cross-sectional side view of the needle of FIG. 2 being partially extracted or partially inserted relative to the cannula of FIG. 1 including the valve structure in the closed position;

FIG. 5 is a cross-sectional side view of the cannula of FIG. 1 including the valve structure in the open position and having its associated syringe attached thereto;

DETAILED DESCRIPTION OF THE PRESENT INVENTION

During a thoracentesis procedure, a catheter or needle is positioned into the pleural cavity of a patient between the parietal and visceral layers of the pleura to remove a collection of body fluid which may be in the pleural cavity due to a number of reasons, such as infection, heart failure, or cancer. Various devices are provided for aspirating the fluid from the pleural cavity through the catheter or needle.

A thoracentesis is the procedure during which fluid located in the pleural cavity is extracted for testing and analysis thereafter. The tapping of pleural fluid is a relatively safe, simple, and commonly used procedure in medical practice. Numerous devices, both homemade and commercially available, are used for such purpose. However, the success of the procedure depends on patient cooperation and physician skill. A commonly feared complication of the procedure is a pneumothorax resulting either secondary to laceration of the lung surface with the sharp edge of a needle or from the sucking of air from a less than air tight system. Since the pleural cavity has a negative pressure relative to atmospheric pressure, it is predisposed to the sucking of air into it if the system or technique used is not airtight. A thoracentesis needle should have the following features: the distal end or the part inserted into the chest cavity should be blunt to avoid accidental laceration of the lung surface by over penetration with the needle, by expansion of the lung by the patient during coughing, or by the repositioning of the lung if the patient were to suddenly move; the outer portion of the needle should be simple to operate and should provide an effective seal to keep air from entering the pleural cavity; and the needle should be economical to manufacture.

Figure 1:
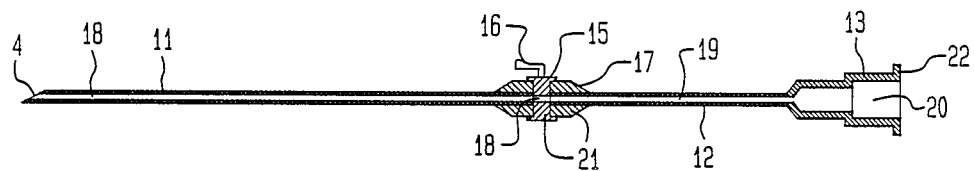
FIG. 1 is a cross-sectional side view of a cannula including its valve structure in the open position and being adapted to perform a thoracentesis procedure according to the present invention.

FIG. 1 is a cross-sectional side view of outer cannula 10 including valve structure 21 in the open position and being adapted to perform a thoracentesis procedure according to the present invention. FIG. 1 shows cannula 10 including: distal longitudinally directed cylindrical hollow portion 11 with lumen 18 and further including distal end 14; proximal longitudinally directed cylindrical hollow portion 12 with lumen 19 and further including proximal end 13 with mechanical attachment means 22 and frictional attachment means 20; and intermediate valve structure 21 including transverse cylindrical rotating member 15 with lumen 23, rotating means 16, and means 17 for securing valve structure 21 to portions 11 and 12. Portion 11 may be about three inches long; portions 11 and 12 may be made of fourteen gauge material; cannula 10 may be about five and one-half inches long; and proximal end 13 including mechanical attachment means 22 and frictional attachment means 20 may be of the so-called Luer-Lok type being adaptable to accept a syringe, stopcock, or drainage attachments. The open position occurs when valve structure lumen 23 is coincident and continuous with cannula lumens 19 and 18. Distal end 14 is of the blunt annular circular type.

Figure 2:
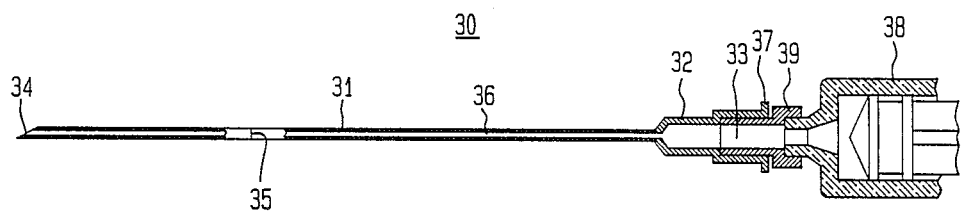
FIG. 2 is a partially cross-sectional side view of the needle including its associated syringe to be used in conjunction with the cannula of FIG. 1.

FIG. 2 is a partially cross-sectional side view of inner needle 30 including associated syringe 38 attached thereto to be used in conjunction with cannula 10 of Figure 1. FIG. 2 shows needle 30 including: distal longitudinally directed cylindrical hollow portion 31 with lumen 36 and further including location surface marker 35, distal end 34, and proximal end 32 with mechanical attachment means 37 and frictional attachment means 33; and syringe 38 further including distal attachment means 39. Portion 31 may be about six inches long and may be made of sixteen gauge material; distal end 34 may be a so-called bevel pointed or slanted annular elliptical end and may be about one-eighth of an inch long; and proximal end 32 may be of the so-called Luer-Lok type.

FIG. 3 is a cross-sectional side view of needle 30 of FIG. 2 being fully inserted into cannula 10 of FIG. 1 including valve structure 21 in the open position. FIG. 3 shows: portion 11 including distal end 14 inserted through chest wall 100 and into pleural cavity 101; portion 31 including distal end 34 also inserted through chest wall 100 and into pleural cavity 101; valve structure 21 including rotating means 16 in the open position; portion 12 including proximal end 13; and syringe 38 including distal end 39 attached to proximal end 32.

FIG. 4 is a partially cross-sectional side view of needle 30 of FIG. 2 being partially extracted or partially inserted relative to cannula 10 of FIG. 1 including valve structure 21 in the closed position. The closed position occurs when valve structure lumen 23 is perpendicular to and not continuous with cannula lumens 19 and 18. FIG. 4 shows: portion 11 including distal end 14 inserted through chest wall 100 and into pleural cavity 101; valve structure 21 including rotating means 16 in the closed position; portion 12 including proximal end 13; portion 31 including distal end 34 inserted into portion 12, location surface marker 35 just being visible proximally, and proximal end 32; and syringe 38 including distal end 39 attached to proximal end 32.

FIG. 5 is a cross-sectional side view of cannula 10 of FIG. 1 including valve structure 21 in the open position and having syringe 38 attached thereto. FIG. 5 shows: portion 11 including distal end 14 inserted through chest wall 100 and into pleural cavity 101; valve structure 21 including rotating means 16 in the open position; portion 12 including proximal end 13; and syringe 38 including distal end 39 attached to proximal end 13.

Figure 6:
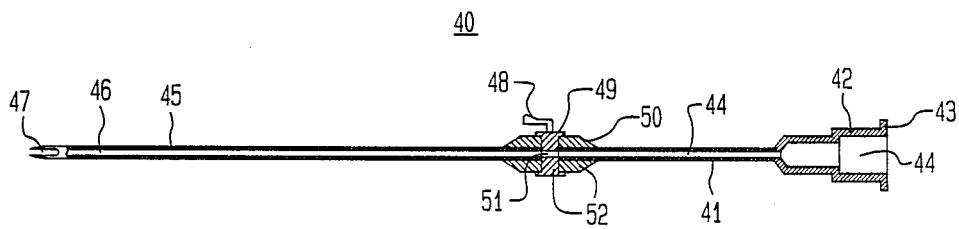
FIG. 6 is a cross-sectional side view of another cannula including its valve structure in the open position and being adapted to perform a pleural biopsy procedure according to the present invention.

FIG. 6 is a cross-sectional side view of outer cannula 40 including valve structure 52 in the open position and being adapted to perform a pleural biopsy procedure according to the present invention. FIG. 6 shows cannula 40 including: distal longitudinally directed cylindrical hollow portion 45 with lumen 46 and further including distal end 47; valve structure 52 further including rotating means 48, transverse cylindrical rotating member 49 with lumen 51, and means 50 for attaching valve structure 52 to portions 45 and 41; and proximal longitudinally directed cylindrical hollow portion 41 with lumen 44 and further including proximal end 42 with attachment means 43 and frictional attachment means 144. Portion 45 may be about three inches long and may include external surface markers spaced about ¼ inch apart for locating the portion of cannula 40 relative to pleural cavity 101; portion 41 may be about one and one-half inches long; portions 45 and 41 may be made of eleven gauge material; proximal end 42 may be of so-called Leur-Lok type; and distal end 47 may be a tapered circular end with a sharp cutting edge.

Figure 7:
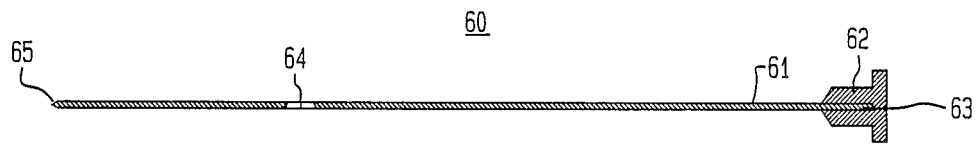
FIG. 7 is a partially cross-sectional side view of the stylet to be used in conjunction with the cannula of FIG. 6.

FIG. 7 is a partially cross-sectional side view of inner stylet 60 to be used in conjunction with cannula 40 of FIG. 6. FIG. 7 shows stylet 60 including: distal longitudinally directed cylindrical solid portion 61 further including location surface marker 64 and distal end 65; and proximal end 62 further including attachment means 63. Portion 61 may be made of thirteen gauge material and may be about six inches long; and distal end 65 may be of the so-called symmetrical trocar point type.

Figure 8:
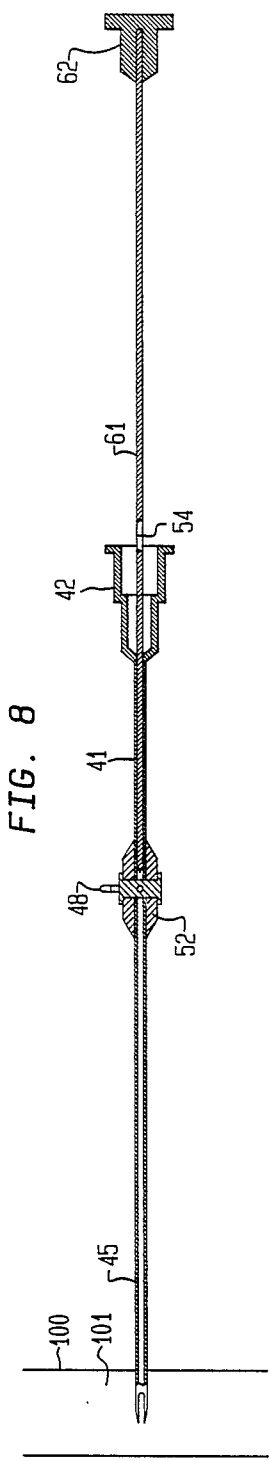
FIG. 8 is a partially cross-sectional side view of the stylet of FIG. 7 being partially inserted or partially extracted relative to the cannula of FIG. 6 including the valve structure in the closed position.

FIG. 8 is a partially cross-sectional side view of stylet 60 of FIG. 7 being partially inserted or partially extracted relative to cannula 40 of FIG. 6 including valve structure 52 in the closed position. FIG. 8 shows: portion 45 including distal end 47 inserted through chest wall 100 and into pleural cavity 101; valve structure 52 including rotating means 48 in the closed position; portion 41 including proximal end 42; portion 61 including distal end 65 inserted into portion 41, location surface marker 64 just being visible proximally, and proximal end 62 further including attachment means 63.

Figure 9:
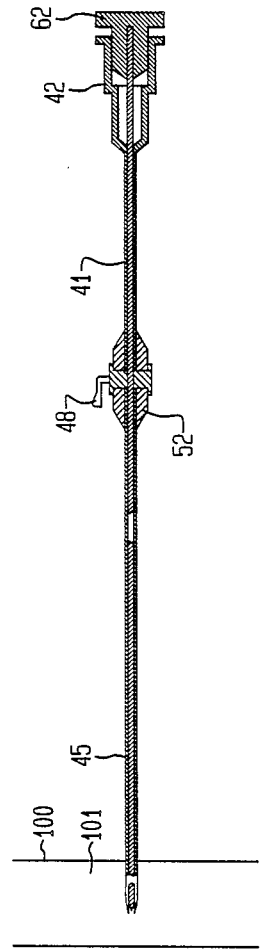
FIG. 9 is a cross-sectional side view of the stylet of FIG. 7 being fully inserted into the cannula of Figure 6 including the valve structure in the open position.

FIG. 9 is a cross-sectional side view of stylet 60 of FIG. 7 being fully inserted into cannula 40 of FIG. 6 including valve structure 52 in the open position. FIG. 9 shows: portion 45 including distal end 47 inserted through chest wall 100 and into pleural cavity 101; valve structure 52 including rotating means 48 in the open position; portion 41 including proximal end 42; and proximal end 62 including attachment means 63.

Figure 10:
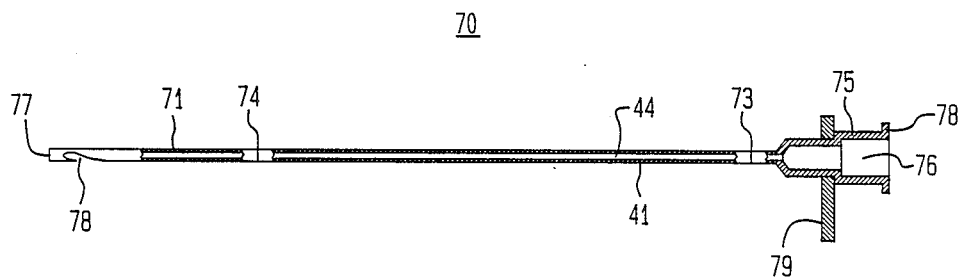
FIG. 10 is a partially cross-sectional side view of the cutting needle to be used in conjunction with the cannula of FIG. 6.

FIG. 10 is a partially cross-sectional side view of inner cutting needle 70 to be used in conjunction with cannula 40 of FIG. 6. FIG. 10 shows cutting needle 70 including: distal longitudinally directed cylindrical hollow portion 71 with lumen 72 and further including proximal location surface marker 73, distal location surface marker 74, distal end 77, and curved lateral cutting edge 78; and proximal end 75 including cutting edge location marker 79, frictional attachment means 76, and mechanical attachment means 78. Portion 71 may be made of thirteen gauge material and may be about five and one-half inches long; cutting edge 78 may be of the so-called sharp hooking snare type; and distal end 77 may of the circular annular type.

Figure 11:
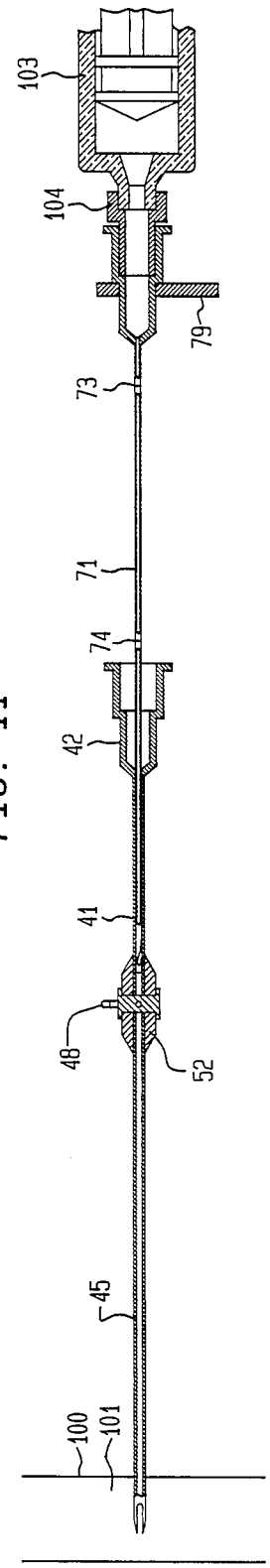
FIG. 11 is a partially cross-sectional side view of the cutting needle of FIG. 10 being partially inserted or partially extracted relative to the cannula of FIG. 6 including the valve structure in the closed position.

FIG. 11 is a partially cross-sectional side view of cutting needle 70 of FIG. 10 being partially inserted or partially extracted relative to cannula 40 of FIG. 6 including valve structure 52 in the closed position. Figure 11 shows: portion 45 including distal end 47 inserted through chest wall 100 and into pleural cavity 101; valve structure 52 including rotating means 48 in the closed position; portion 41 including proximal end 42; portion 71 including distal end 77 and cutting edge 78 being inserted into portion 41, distal location surface marker 74 just being visible proximally, proximal location surface marker 73, and proximal end 75 with mechanical attachment means 78 being attached to distal end 104 of syringe 103.

Figure 12:
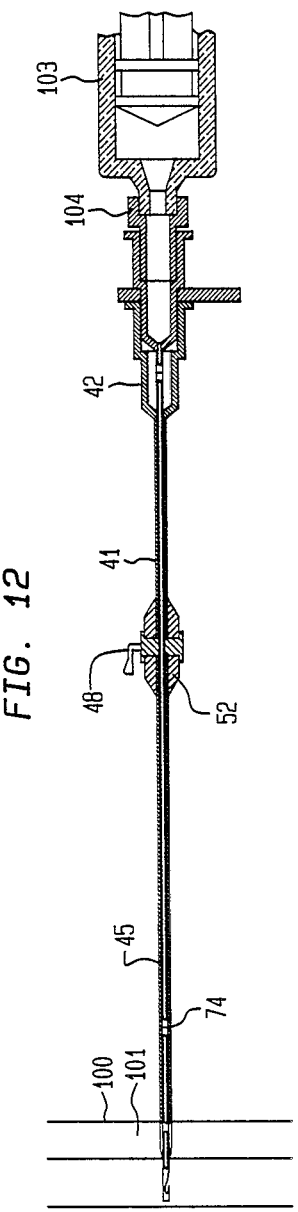
FIG. 12 is a cross-sectional side view of the cutting needle of FIG. 10 being fully inserted into the cannula of FIG. 6 including the valve structure in the open position.

FIG. 12 is a cross-sectional side view of cutting needle 70 of FIG. 10 being fully inserted into cannula 40 of FIG. 6 including valve structure 52 in the open position.

FIG. 12 shows: portion 45 including distal end 47 inserted through chest wall 100 and into pleural cavity 101; valve structure 52 including rotating means 48 in the open position; portion 41 including proximal end 42; portion 71 including both distal end 77 and cutting edge 78 just being visible distally; and proximal end 75 including mechanical attachment means 78 being attached to distal end 104 of syringe 103.

Figure 13:
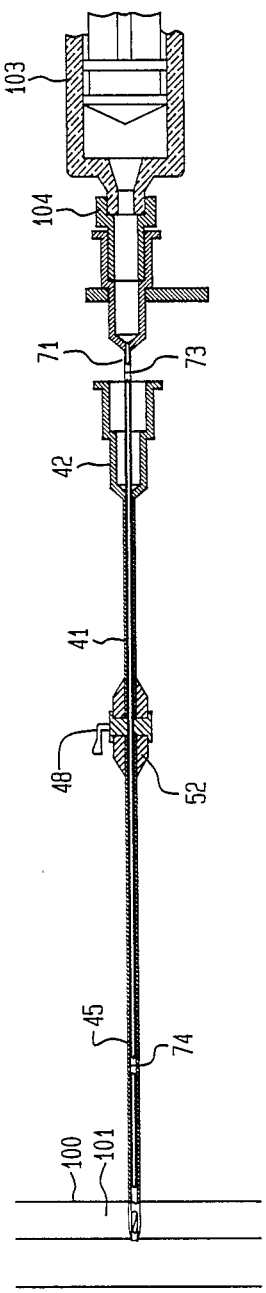
FIG. 13 is a partially cross-sectional side view of the cutting needle of FIG. 10 being inserted into the cannula of FIG. 6 and the cannula being in its further advanced position relative to the cutting needle and including the valve structure in the open position.

FIG. 13 is a partially cross-sectional side view of cutting needle 70 of FIG. 10 inserted into cannula 40 of FIG. 6 and cannula 40 being in its further advanced position relative to cutting needle 70 and including valve structure 52 in the open position. FIG. 13 shows: portion 45 including distal end 47 inserted through chest wall 100 in its further advanced position to again cover distal end 77 and cutting edge 78 having the biopsied tissue attached thereto; valve structure 52 including rotating means 48 in the open position; portion 41 including proximal end 42; portion 71 including proximal location surface marker 73 just being visible proximally; and proximal end 75 including mechanical attachment means 78 attached to distal end 104 of syringe 103.

The valve structure and associated instrument elements required for effecting the thoracentesis procedure according to the present invention comprises: an outer hollow cannula including a valve structure; and an inner hollow needle for fitting into such cannula as tight as possible. In the open position of the valve structure, the cannula lumen is concentric with the valve structure lumen; while in the closed position of the valve structure, the valve structure lumen is perpendicular to the cannula lumen.

For performing the thoracentesis procedure according to the present invention, the patient is prepped in the usual manner and the thoracentesis site is determined. A local anesthesic is then applied. Thereafter, a one millimeter incision may made with a number eleven scalpel to help facilitate penetration of the cannula-needle combination into the chest wall. The overall structure in the pre-penetration configuration comprises: cannula 10 including valve structure 21 in the open position; needle 30 being fully inserted therethrough such that needle distal end 34 is just distal to cannula distal end 14; and syringe 38 being attached to needle proximal end 32. Distal ends 34 and 14 are then advanced through chest wall 100 and into pleural cavity 101 while needle 30 is aspirated with syringe 38. Once outward pleural fluid flow is encountered and achieved, cannula 10 is further advanced appoximately ½ to 1 centimeter into pleural cavity 101 to cover distal end 34 of needle 30. See FIG. 3. Then, with cannula 10 well secured in place, needle 30 is slowly withdrawn or extracted from cannula 10 while gentle aspiration of the fluid is maintained with syringe 38. This extraction process is continued until approximately the distal two inches of needle 30 is located in the proximal two inches of cannula 10. This can be assured via location surface marker 35 which is correctly located on the outer surface of needle 30 and is just visible proximally in this position. This is done to assure that distal end 34 is not still inside or distal to valve structure 21. At this time, valve structure 21 is placed in the closed position in order to occlude distal portion 11 of cannula 10. See FIG. 4. The procedure so far eliminates the probability of allowing an air leak into pleural cavity 101. At this time, needle 30 can be fully withdrawn from cannula 10 without there being a leak into pleural cavity 101. The pleural fluid so far collected in syringe 38 can be tested and analyzed. Cannula 10 can now be maintained inserted into pleural cavity 101 with valve structure 21 in the closed position. Inserted cannula 10 including valve structure 21 in the closed position can now be utilized alternatively as follows: a large syringe 38 may be attached to proximal end 13 of cannula 10; valve structure 21 may then be placed in the open position; and then large amounts of fluid may be aspirated from chest cavity 101. See FIG. 5. Once such aspiration procedure is completed, valve structure 21 is placed in the closed position and syringe 38 may be removed or detached from proximal end 13 of inserted cannula 10. This procedure can be repeated as many times as necessary. Alternatively, intravenous tubing can be attached to proximal end 13 of inserted cannula 10 including valve structure 21 in the closed position; the tubing must be clamped completely; an associated vacuum bottle is then pierced with the needle associated with the other end of the intravenous tubing; valve structure 21 is placed in the open position and such tubing is unclamped. Fluid will now flow automatically into the vacuum bottle and the flow can be controlled by the extent of clamping of the intravenous tubing. It will be apparent that this overall procedure can also be useful for the instilling of sclerosing agents or chemotherapeutic agents into chest cavity 101. At the completion of the overall procedure, inserted cannula 10 is then pulled out from pleural cavity 101 and the puncture site is closed using antibacterial ointment and adhesive bandages.

Several biopsy needles are available for the taking of percutaneous biopsy samples of the pleura. None of these available biopsy needles provides both high yield and safety. The present instrument provides such advantages with relative simplicity. Since the pleural cavity is under negative pressure, it is of utmost importance that an airtight system be provided. The biopsy medical instrument according to the present invention comprises: an outer hollow cannula including a valve structure; an inner solid stylet; and an inner hollow cutting needle. The valve structure includes a rotating valve member with a through lumen which is perpendicular to the axis of rotation of the rotating valve member and which through lumen can be rotated to be perpendicular to the cannula lumen into the closed position or can be rotated to be concentric with the cannula lumen into the open position. The diameter of the cannula lumen is equal to the diameter of the rotating valve member lumen. The stylet is adaptable to fit completely into the cannula except for its proximal end which is adapted to fit into the cannula proximal end. The stylet includes a sharp symmetrical distal end which is adapted to coincide with the sharp distal end of the cannula. The cutting needle is adapted to fit into the cannula with about one centimeter of the cutting needle distal end being exposable beyond the distal end of the cannula. Such exposed cutting needle distal end includes an annular circular cross-section and just proximal to such distal end it includes the functional lateral cutting edge. The most proximal end of the cutting needle internally includes a cylindrical surface which is adaptable to frictionally receive the distal end of a syringe with or without mechanically locking onto same. The cutting needle proximal end also includes laterally extending means for locating and coordinating the rotated angular position of the needle cutting edge. The cutting needle also includes proximal and distal location surface markers on its external surface for cuing the longitudinal position of the cutting needle along the cannula lumen. The stylet and the cutting needle both include location surface markers to indicate that each element when inserted into the cannula is just proximal to the location of the cannula valve structure while the cutting needle alone includes a location surface marker to indicate that the cutting needle distal end is immediately adjacent to the cannula distal end. The cannula also includes attachment means at its proximal end to allow the attachment of a syringe or intravenous tubing to drain fluid from the pleural cavity. The distal 3 inches of the cannula may include markers being about ½ inch apart to help locate the position of the cannula relative to the pleural cavity.

The steps for performing the pleural biopsy procedure according to the present invention are as follows. The appropriate intercostal space for the pleural biopsy is identified. The location of such space is confirmed by draining fluid using a syringe with a needle. After applying adequate local anesthesia to the penetration site, a cut is made on the skin and the subcutaneous tissue with a size eleven scalpel. The cut should be big enough to allow entry of the pleural biopsy needle into the pleural space. In the initial insertion step, the combination comprising cannula 40 including valve structure 52 in the open position and stylet 60 inserted therein is inserted into the cut and into the pleural space. See FIG. 9. Once the pleural space is reached, then cannula 40 with valve structure 52 in the open position is held in place while stylet 60 is extracted until location surface marker 64 on stylet 60 is just visible proximally. See FIG. 8. This indicates that distal end 65 of stylet 60 is just proximal to valve structure 52. At this time, valve structure 52 is placed in the closed position so that there is no further communication of distal portion 45 of cannula 40 with the atmosphere. This configuration allows for an effective seal from the atmosphere. Stylet 60 is now completely extracted from cannula 40. Next, cutting needle 70 is inserted into cannula 40 until distal location surface marker 74 on cutting needle 70 is just visible proximally. Inserted cutting needle 70 and its associated syringe 103 provide an effective seal in this configuration. See FIG. 11. Now, valve structure 52 is placed in the open position and cutting needle 70 is pushed completely into cannula 40 until distal end 77 of cutting needle 70 is distal to distal end 47 of cannula 40. Proximal cutting edge location marker 79 is immediately adjacent to proximal end 42. See FIG. 12. Next, some pleural fluid is suctioned into attached syringe 103 to make sure that distal end 77 of cutting needle 70 is in pleural space 101. Next, cutting edge 78 of cutting needle 70 is hinged against the adjacent parietal pleura and some more pleural fluid is suctioned with syringe 103 to make sure that distal end 77 of cutting needle 70 is in pleural space 101. Next, cannula 40 is slid forward with cutting needle 70 being held in place manually relative to the parietal pleura until proximal location surface marker 73 of cutting needle 70 is just visible proximally thereby indicating that distal end 47 of cannula 40 fully covers distal end 77 of cutting needle 70. During this step, the piece of parietal pleura that is cut off remains stuck within cutting edge 78 of cutting needle 70. See FIG. 13. Next, cutting needle 70 is extracted enough from cannula 40 so that distal location surface marker 74 of cutting needle 70 is just visible proximally. Valve structure 52 is then placed in the closed position thereby closing the communication of distal portion 45 of cannula 40 to the atmosphere. See FIG. 11. Next, cutting needle 70 is fully withdrawn from cannula 40 and the biopsied pleural tissue is removed from cutting edge 78 and is placed in an appropriate receptacle.

While the arrangement according to the present invention has been described in terms of a specific illustrative embodiment, it will be apparent to those skilled in the art that many modifications are possible within the spirit and scope of the disclosed principle.

What is claimed is:

1. A method for penetrating external body tissue and for taking a sample of internal body tissue being located below such external body tissue, said method comprising the steps of:
   a. penetrating such external body tissue with a cannula-stylet combination, said combination comprising an outer hollow cannula and an inner solid stylet; said cannula including a valve structure, a proximal end portion, and a distal end portion; said cannula distal end portion being longer than said cannula proximal end portion and said valve structure combined; said cannula distal end portion further including a symmetrically tapered circular sharp edge; said stylet including a proximal end portion and a distal end portion; said stylet distal end portion further including a location surface marker and a symmetrically tapered pointed edge; said valve structure being in the open position and said stylet distal end portion being located just distal to said cannula distal end portion;
   b. withdrawing said stylet from said cannula while maintaining said cannula distal end portion located within such internal tissue until said stylet distal end portion location surface marker is located just proximal to said cannula proximal end portion whereby said stylet distal end portion is located just proximal to said valve structure;
   c. placing said valve structure in the closed position;
   d. fully withdrawing said stylet from said cannula;
   e. inserting an inner hollow needle-syringe combination into said cannula; said needle including a proximal end portion and a distal end portion; said needle proximal end portion further including a location surface marker; said needle distal end portion further including a location surface marker, sharp lateral edge cutting means, and a circular annular surface; said syringe being attached to said needle proximal end portion; wherein said needle distal end portion location surface marker is located just proximal to said cannula proximal end portion whereby said needle distal end portion is located just proximal to said valve structure and within said cannula proximal end portion;
   f. placing said valve structure in the open position;
   g. inserting said needle until said proximal end portion location surface marker is located immediately adjacent to the cannula proximal end, whereby said needle distal end portion protrudes beyond said cannula distal end;
   h. aspirating any fluid being located just proximal to such internal tissue using said syringe being attached to said needle proximal end portion;
   i. obtaining a piece of such internal tissue using said needle distal end portion sharp lateral edge cutting means while further aspirating such fluid using said syringe being attached to said needle proximal end portion;
   j. advancing said cannula distally relative to said needle such that said needle distal end portion is covered by said cannula distal end portion;

k. withdrawing said needle from said cannula until said needle proximal end location surface marker is located just proximal to said cannula proximal end portion whereby said needle distal end portion is just proximal to said valve structure;

l. placing said valve structure in the closed position; and m. fully withdrawing said needle including such piece of attached internal tissue from said cannula having said valve structure in the closed position.

* * * * *